(12) United States Patent
O'Shea

(10) Patent No.: US 6,718,984 B2
(45) Date of Patent: Apr. 13, 2004

(54) SUSPECT RESTRAINING DEVICE

(76) Inventor: John O'Shea, 5525 N. Paris, Chicago, IL (US) 60656

( * ) Notice: Subject to any disclaimer, the term of this patent is extended or adjusted under 35 U.S.C. 154(b) by 189 days.

(21) Appl. No.: 09/910,410

(22) Filed: Jul. 23, 2001

(65) Prior Publication Data

US 2003/0015204 A1 Jan. 23, 2003

(51) Int. Cl.[7] .................................................. A61F 5/37
(52) U.S. Cl. ........................ 128/846; 128/869; 128/876
(58) Field of Search .............................. 128/845, 846, 128/869, 870, 876; 5/81 R, 424; 297/484; 70/16

(56) References Cited

U.S. PATENT DOCUMENTS

| 3,545,237 | A |   | 12/1970 | Thompson |         |
|-----------|---|---|---------|----------|---------|
| 4,122,587 | A |   | 10/1978 | Weiss    |         |
| 4,386,605 | A |   | 6/1983  | Wong     |         |
| 4,846,527 | A | * | 7/1989  | Julien et al. | 297/411 |
| 5,492,285 | A | * | 2/1996  | Hamrick  | 128/876 |
| 5,546,962 | A |   | 8/1996  | Power    |         |
| 5,738,112 | A | * | 4/1998  | Brod     | 128/869 |
| 5,875,781 | A |   | 3/1999  | Klaus    |         |

\* cited by examiner

*Primary Examiner*—Michael A. Brown
(74) *Attorney, Agent, or Firm*—Patnaude & Videbeck

(57) ABSTRACT

A suspect restraining device is disclosed that includes a device for extending and retracting a plastic-covered cable from one end of a housing and inserting the end of the cable in another end of the housing to selectably releaseably retain that end in the housing. When the free end of the cable is retained in the housing, the opposing end of the cable is restrained in its movement to only allow retraction of the cable into the housing, thus snugly fitting the cable around the torso of a suspect to be detained. The housing may be mounted in vertical position on the wall of a building or on the inside of a police wagon or corrections vehicle or on the outside of a police squad car.

12 Claims, 6 Drawing Sheets

SUSPECT RESTRAINING DEVICE

This invention relates to devices for restraining human beings, and more particularly, to a device used by police officers or correctional officers to extend around the trunk of an individual being restrained.

BACKGROUND OF THE INVENTION

Devices for restraining people generally have two types of uses, the first is for restraining patients in a hospital, usually on a bed or gurney. The second is restraining devices used by police officers or correctional officers to physically detain suspects or handcuff them.

U.S. Pat. No. 4,122,587 issued to Weiss et al on Oct. 31, 1978 discloses a hold down device for securing a patient on an X-ray or other examination table, and U.S. Pat. No. 5,875,781 to Klaus issued Mar. 2, 1999 discloses a shoulder harness for use in positioning patients while lying on a table.

With respect to restraining suspects or prisoners, U.S. Pat. No. 4,386,605 discloses a capture and restraining device that is meant to tie a suspect's arms and legs, and U.S. Pat. No. 5,546,962 discloses the use of a manacle by connecting that manacle to a stationary tubular device. The device also discloses a plastic ratchetable tie that operates to tighten in one direction but not loosen. These types of ties have been molded to form hand cuffs made of polytetrafluoroethylene or generally sold under the TEFLON brand.

Generally, hand cuffs or manacles will prevent a suspect or a person being detained from using their hands, but not their other extremities. If a policeman or correctional officer needs to detain several individuals, there is nothing inherent in the hand cuffs to prevent the individual from moving, especially if the police officer or corrections officer turns their back on that individual. While the Power patent discloses a means of connecting an individual to an external member, it appears that it is only useful for connecting that individual to a tubular member that may or may not be in the general area in which the police officer or correctional officer is located.

The Thompson et al U.S. Pat. No. 3,545,237 discloses an electrically power activated manacle that is mountable, as shown in the patent, on the roof of a police car and acts in an electronic manner similarly to older stocks or pillories used in Colonial times with the suspect's hands positioned through recesses in the unit, and then metal arms are electrically moved to close over the tops of the recesses and secure the suspect's wrists therein.

A need has developed for a suspect restraining device that is capable of restraining an individual at a desired location or position while acting independently of but complementary of a pair of hand cuffs or manacles. Additionally, a need has developed for restraining a suspect or individual to a desired position or location that can be utilized both on police or correction vehicles, and also in police stations, correctional facilities or the like.

It is, therefore, an object of the present invention generally stated, to provide an improved means for restraining a suspect by restraining movement of the torso of an individual.

Another object of the present invention is a suspect torso restraining device that acts complementary to the use of hand cuffs or manacles.

Another object of the present invention is the use of a torso restraining device that is mountable on mobile police or correction vehicles and is also mountable on the walls of police stations or correction facilities.

SUMMARY OF THE INVENTION

The invention resides in a restraining device for use by law enforcement personnel to detain persons. The device comprises an elongate base having first and second opposed ends which is adapted for fixed mounting on an external object. A cover is mountable over the base, including first and second apertures therethrough, with each aperture positioned adjacent one of the first and second opposed ends of the elongate base. An elongate resilient rod-like member having first and second opposed ends is mounted on the frame for selectably releaseably withdrawing the resilient rod-like member through the first aperture on the cover. Selectably releasable securing means are mounted on the base adjacent the second aperture for receiving and retaining the first end of the resilient rod-like member thereon.

BRIEF DESCRIPTION OF THE DRAWINGS

The features of the present invention which are believed to be novel are set forth in the attached claims. The invention may best be understood by reference to the following description taken in conjunction with the accompanying drawings in which like numerals refer to like parts, and in which:

DETAILED DESCRIPTION OF THE PREFERRED EMBODIMENTS

Figure 1:
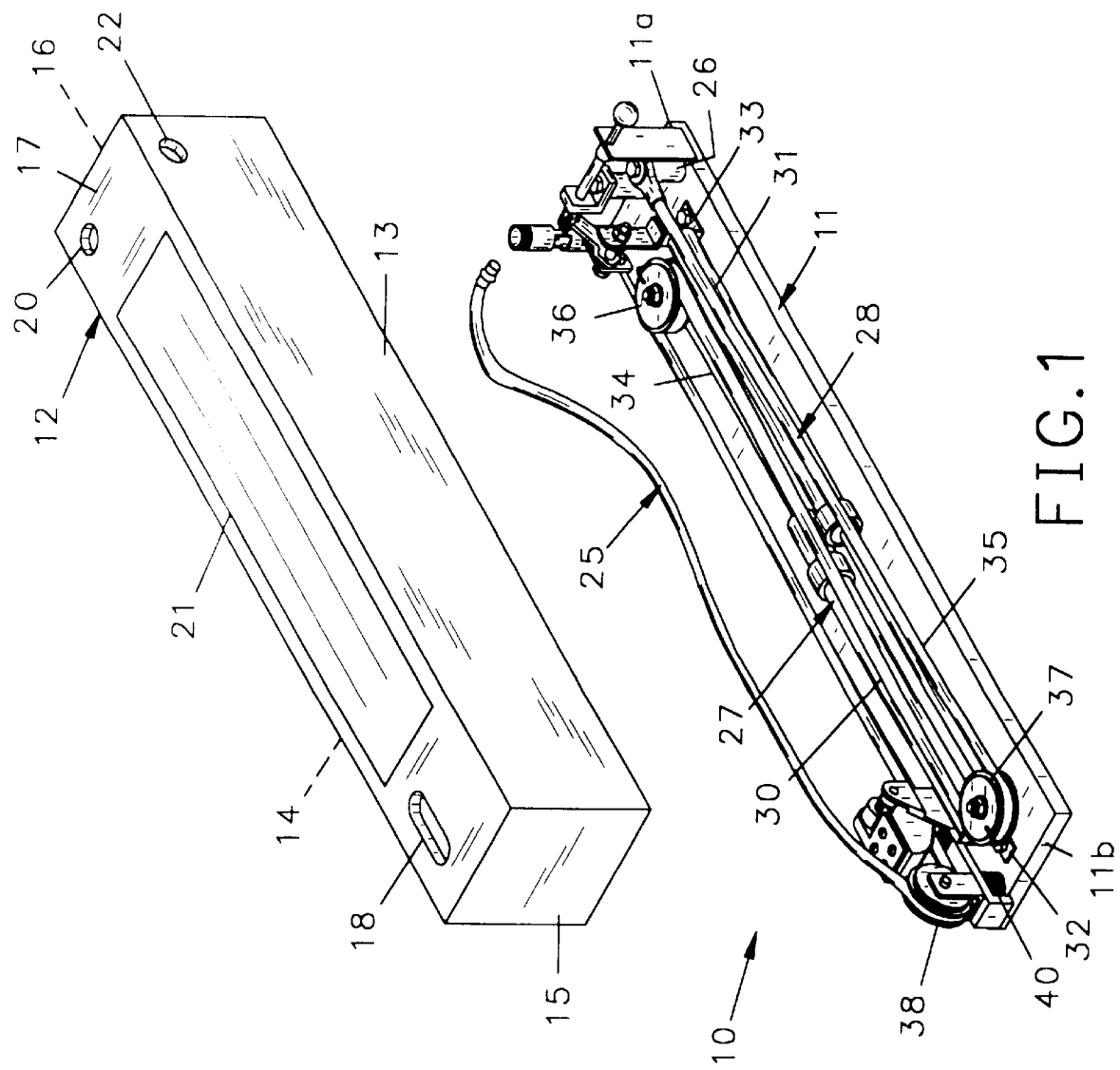
FIG. 1 is a perspective view of a first embodiment of the restraining device, constructed in accordance with the present invention, showing same in a retracted position.

Referring to FIG. 1, a suspect restraining device, generally indicated at 10, constructed in accordance with the present invention, includes a generally rectangular base 11 and a hollow five-sided rectangular cover 12. Top cover 12 securely mounts over the side edges of base 11 to cover the inner mechanism of the restraining device, to be discussed in more detail below. Top cover 12 includes opposed long sides 13 and 14 (not shown) and opposed ends 15 and 16 (not shown). The top 17 of the cover is generally rectangular in shape and includes apertures 18 and 20 at opposing ends thereof along with a non-skid surface 21 extending between the apertures that hinders or prevents the rotation of a suspect's torso is captures in the restraining device. Elongate side 13 includes an aperture 22 adjacent its upper right hand corner that will be discussed in more detail below.

Under the cover 12, the base 11 preferably is a sturdy rectangular metal plate that includes mechanisms for allowing the extension and retraction of a plastic tube covered cable, generally indicated at 25, to extend around the torso of an individual to be restrained. Frame 11 includes a cable receiving and locking end 11a and an extension and retraction end 11b. In this first embodiment of the invention, the cable 25 extends within the cover 12 in a serpentine manner back and forth over the inside of the cover where it begins at a cable mounting 26, positioned adjacent the receiving and retaining end of the base 11a. In this embodiment, a pair of opposed shock absorbers, 27, 28, are mounted on base 11 with their respective base housings 30 and 31 mounted adjacent the extending and retracting end at 32 and adjacent the cable receiving and retaining end at 33, respectively. Actuator rods 34, 35, respectively, extend and are biased outwardly of the respective shock absorber housings 30 and 31. A pulley wheel 36, 37 is rotatably mounted on the distal end of each of the shock absorber actuator rods 34, 35, respectively. A third pulley wheel 38 is rotatably mounted to the rectangular base at mounting 40 positioned adjacent the extending and receiving end 11b of base plate 11.

Figure 2:
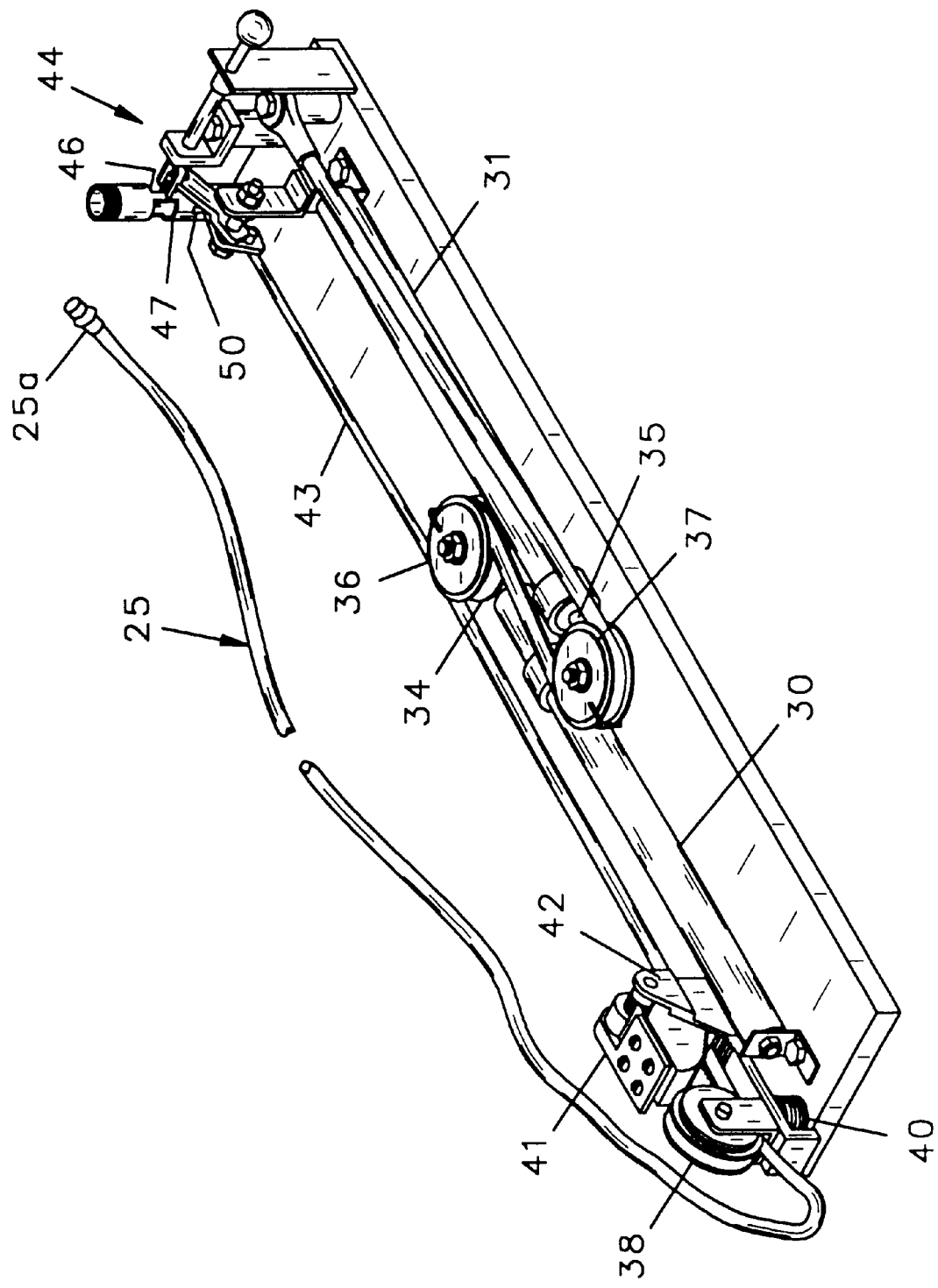
FIG. 2 is a perspective view similar to that shown in FIG. 1 of the restraining device shown in extended position.

Referring to FIG. 2, with the actuator rods 34, 35 withdrawn into their respective shock absorber housings 30, 31, the cable 25 is fully extended in its serpentine path through pulleys 38 and 36 and 37. With the cable in extended position and the pulleys 36 and 37 in their retracted positions, a cable brake mechanism consisting of a rotatable paul 41 rotatably mounted on a trunion device 42 affixed to base 11 by the stationary pulley mounting 40 securely mounts the rotatable paul 41 in position in the path of cable 25 between stationary pulley 38 and movable pulley 36.

A linkage 43 between the rotatable paul 41 and the receiver and retainer mechanism, generally indicated at 44, moves the rotatable paul into cable engaging position when the receiving and retaining mechanism indicates the distal end 25a of the cable is not engaged in the receiving and retaining mechanism 44. The engagement of the rotatable paul 41 on the cable 25 assures that the cable may be pulled outwardly of the cover 12 through aperture 18 to its fully extended position in one direction only, i.e., outwardly. If the cable 25 is released, the teeth of the rotatable paul 41 will engage the cable 25 and not allow it to retract into the mechanism. In an opposite manner, once the distal end 25a of cable 25 is secured on the receiving and retaining mechanism 44, the rotatable paul 41 is moved clockwise in its trunion mount 42 to disengage from the cable 25 allowing it to retract, thus securing the cable around the torso of a suspect to be restrained by the mechanism of the present invention.

Figure 3:
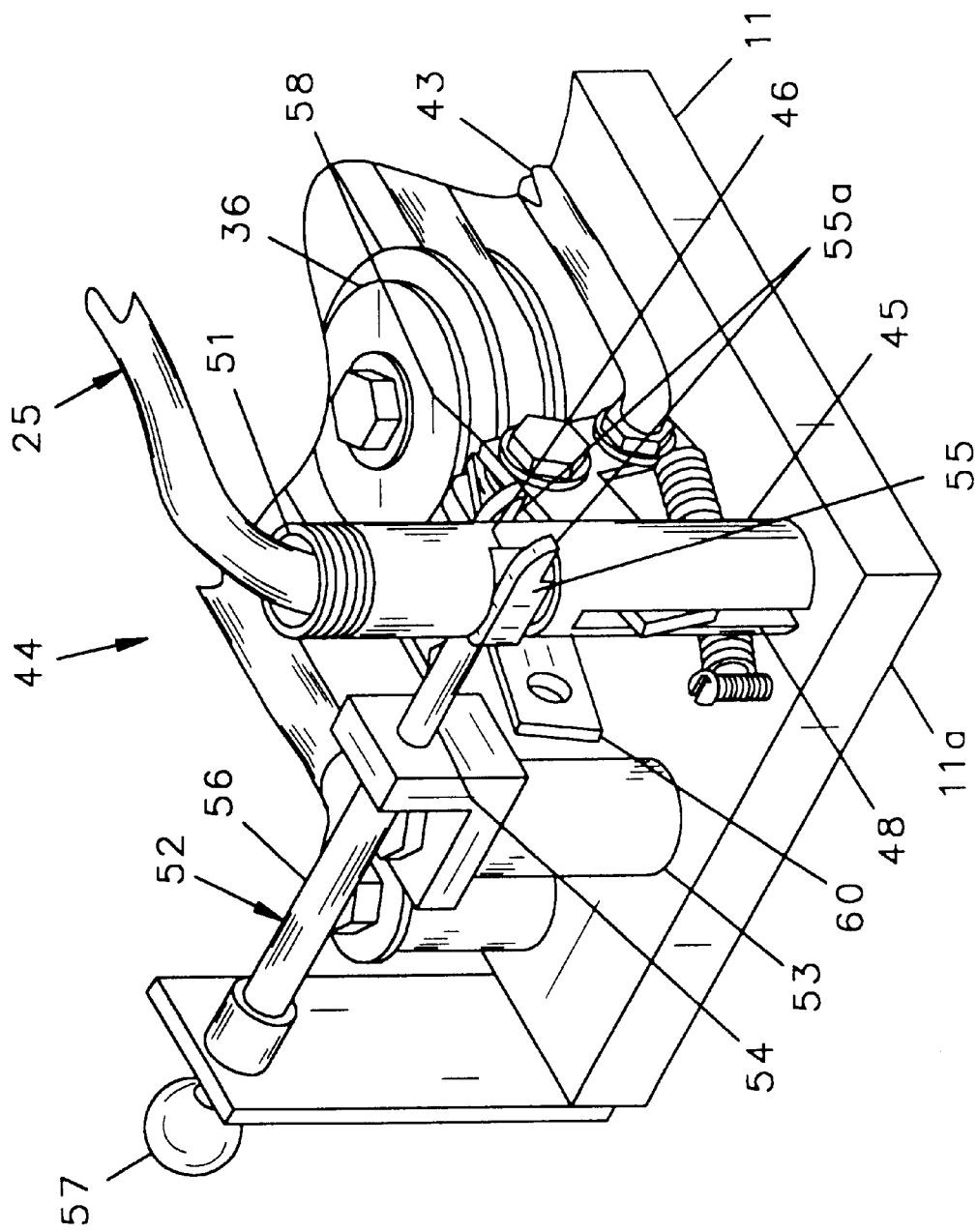
FIG. 3 shows a fragmentary perspective view of the latching mechanism of the first embodiment of the restraining device.

Referring to FIG. 3, the receiving and retaining mechanism, generally indicated at 44, mounted on the receiving and retaining end 11a of base 11 includes a cable receiving tube 45 mounted on base 11. Tube 45 further includes a pair of latch receiving slots 46, 47 (FIG. 2), a pair of lock linking slots 48, 50 (FIG. 2) and a cable receiving tubular top opening 51. The latch mechanism, generally indicated at 52 includes a mounting 53 and, in this embodiment, a spring-loaded (not shown) fork shaped latch 54 with opposed forks 55—55 that extend into and through the latch slots 46, 47, respectively on tube 45. The spring-loaded latch 54 slides through a housing 56 having a biasing spring (not shown) therein and ends in a ball shaped handle 57 in this embodiment, which is intended to extend outwardly of the aperture 22 in the long side 13 of cover 12. It should be noted that for purposes of security, ball handle 57 may be omitted and a shorter latch 54 that does not extend outwardly of the aperture 22 may be fitted on its distal end. The end of that latch may be shaped to receive a removable handle or key type mechanism to operate the latch in a manner so that the persons detained or restrained cannot operate that mechanism.

In operation, when the distal end 25a (FIG. 2) is inserted in the round opening 51 of tubular receiver 45 with the latch 54 in retracted position, after the fat portion of the distal end 25a moves downwardly past slots 46, 47, the latch 54 may be inserted in those slots and closed over distal end 25a to prevent its removal from the tube 45. With the distal end 25a inserted beyond slots 46 and 47, that distal end 25a pushes the crank mechanism 58 to move link 43 and rotate paul 41 (FIG. 2) to release the paul from cable 25 so that the shock absorbers tend to extend their actuator arms 34, 35 and pulleys 36 and 37, respectively, to retract the cable through aperture 18 in cover 12 and thus restrain a person around whose torso the cable 25 is extended. The teeth on the paul 41 allow the cable to be retracted but prevent the cable from extending.

When the latch 54 is retracted from slots 46, 47, notches 55a, 55a in the bottom of latch forks 55—55 catch a second bell crank mechanism 60 and also actuated link rod 43 to allow the cable 25 to be pulled outwardly of the aperture 18 in cover 12 while preventing it from retracting therethrough.

Figure 4:
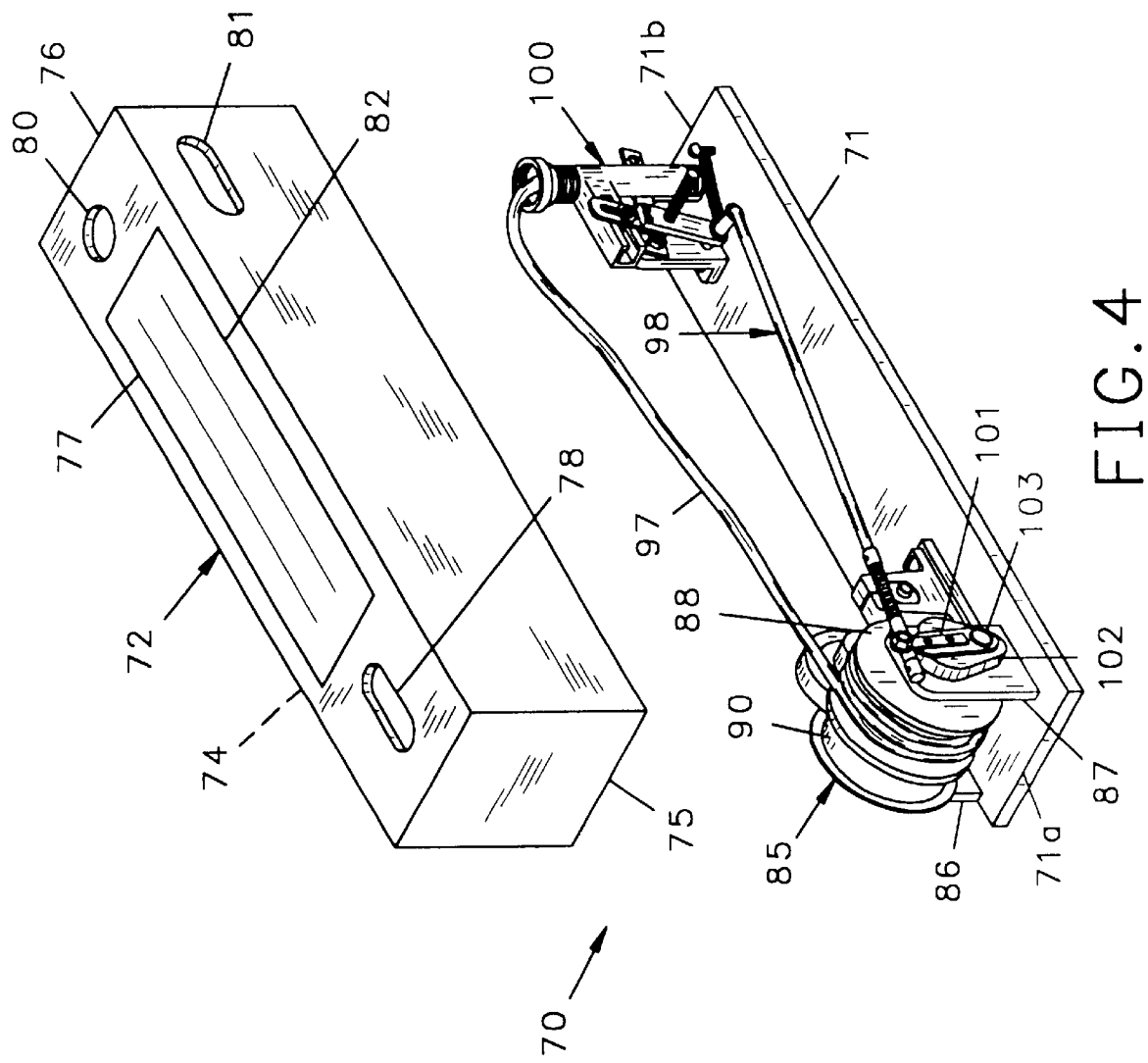
FIG. 4 shows a perspective view of a second embodiment of the restraining device with the distal end of the restraining cable mounted in its receiver.

Referring to FIG. 4, a second embodiment of the present invention, generally indicated at 70, includes a generally rectangular base 71 having a cable mechanism, to be discussed in more detail below, mounted thereon and a hollow rectangular polyhedral cover, generally indicated at 72, sized to fit over the edges of base 71 and be secured thereover. Cover 72 includes opposed long sides 73, 74 opposed ends 75, 76 and a rectangular cover 77 that includes an elongate cable aperture 78 adjacent a first end 75 of cover 72 and a circular cable receiving aperture 80 adjacent the end 76 of cover 72. An elongate aperture 81 is positioned adjacent end 76 of long cover side 73 and will be discussed in more detail below. As in the first embodiment, an anti-skid surface 82 may be positioned on the top surface 77 of cover 72 to prevent a detainee or suspect from turning around while being restrained in the device of the second embodiment 70.

Figure 5:
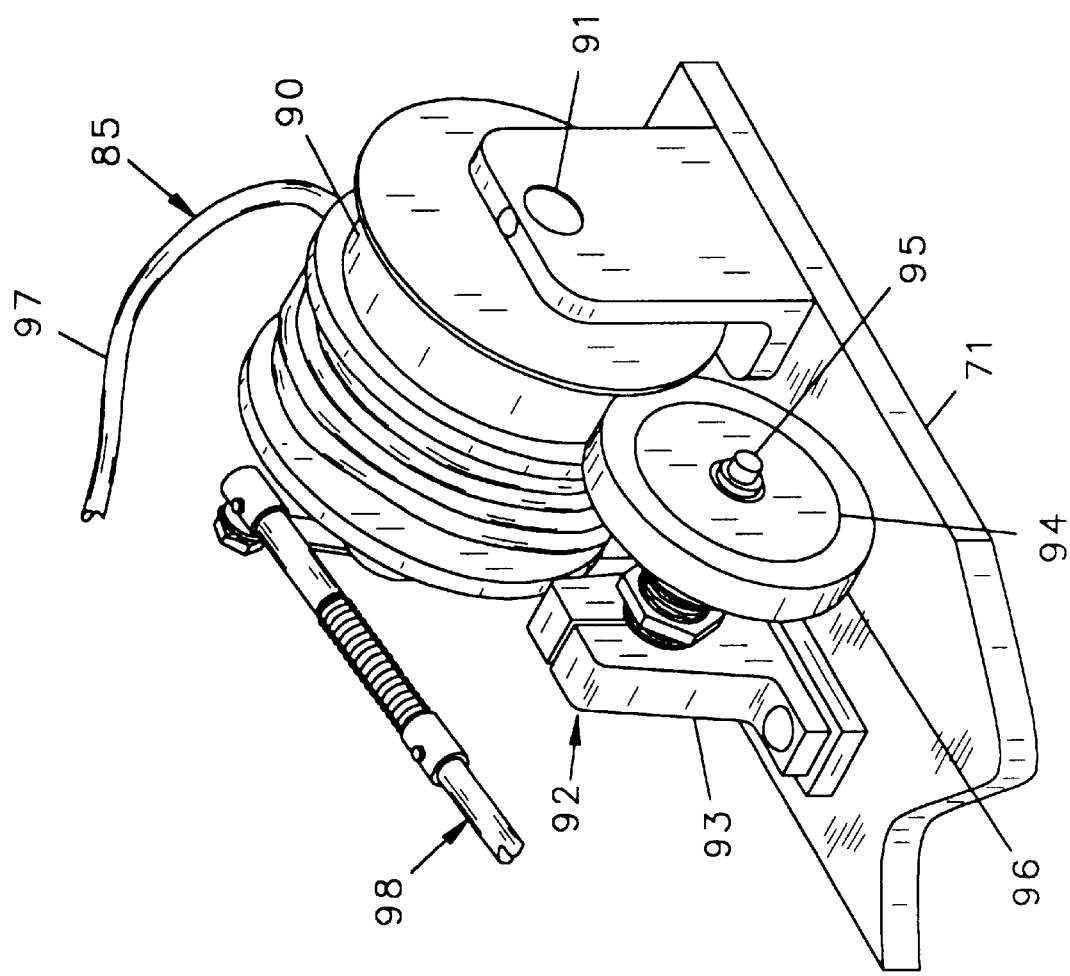
FIG. 5 shows a fragmentary detail perspective view of the reel and clutch of the second embodiment of the present invention.

Referring to FIGS. 4 and 5, a ratchetable reel mechanism, generally indicated at 85 is mounted on trunions 86, 87 that are secured adjacent the reel end 71a on base 71. The reel mechanism 85 includes a two-part drum that includes the cable winding reel 88 and coaxially thereadjacent a clutch receiving reel 90, both axially mounted between the trunions 86 and 87 (on axle 91). As shown most clearly in FIG. 5, a wheel type clutch mechanism, generally indicated at 92 includes a trunion mounting 93 mounted on the base 71 adjacent the reel, and a clutch wheel 94 axially mounted on trunion 93 through axle 95 that includes a rubber annular outer layer 96 which engages the clutch reel 90 to slow the rotational operation of the reel 85. It should be noted that the reel mechanism 85 is spring loaded in the interior thereof (not shown) to automatically retract the cable 97 when desired. Cable 97 is a plastic covered cable similar to cable 25 in the first embodiment and also includes a distal end 97a (FIG. 6) similar to the distal end 25a of the first embodiment.

Figure 6:
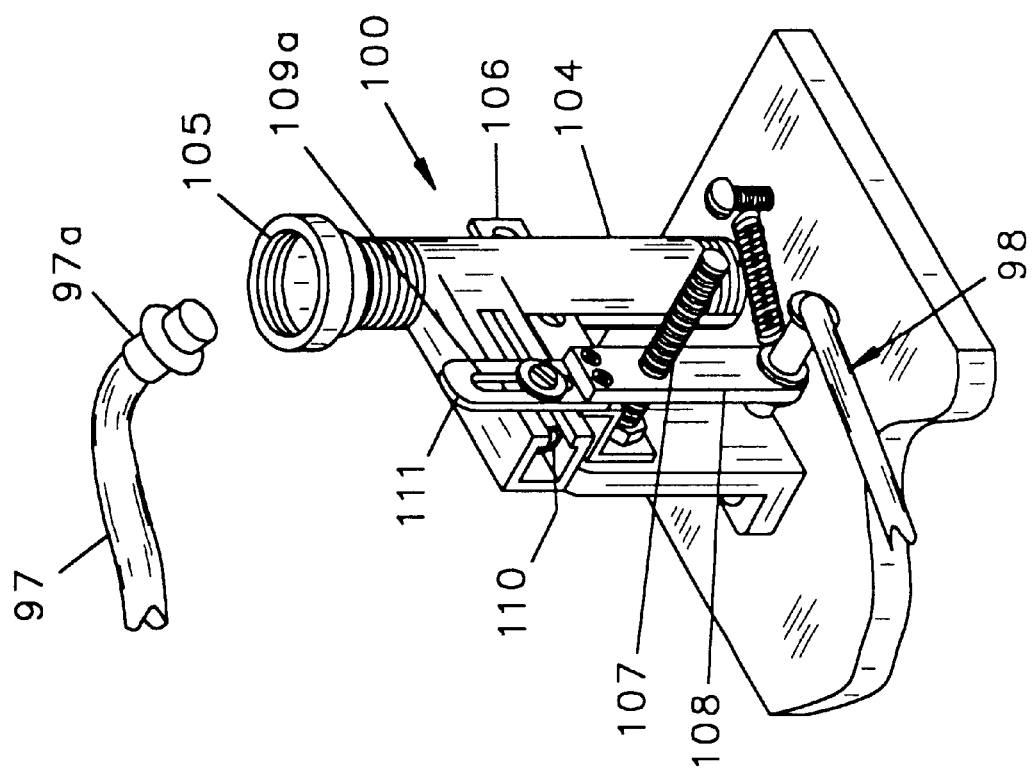
FIG. 6 shows a fragmentary perspective detail view of the receiver for selectably releaseably retaining the free end of the restraining cable.

As with the first embodiment, a linking mechanism, generally indicated at 98, extends between the reel mechanism and the cable receiving mechanism, generally indicated at 100 in FIGS. 4 and 6. As shown most clearly in FIG. 4, linking mechanism 98 is attached and cushioned by springs at its reel end by a lever 101 that is secured to a ratchet mechanism 102. Ratchet mechanism 102 is a mechanism taken from the head of a ratchet for a set of socket hand tools. In this preferred embodiment, the ratchet head 102 includes a ½ inch male socket driving member (not shown) that is received along the rotational axis of the cable receiving end 88 of reel mechanism 85. The bottom end of link 101 is secured at 103 to the direction changing control member for the head of ratchet 102. Axially moving the link 98 pivotally moves the ratchet control lever 103 through link 101 to change the direction of the ratchet mechanism 102 from that of allowing the retraction of cable 97 onto reel 88, to its opposite, allowing the extension of cable 97 from its reel 88, and vice versa.

Referring to FIG. 6, the cable receiving mechanism, generally indicated at 100, includes a cable receiving tube 104 having an open upper end 105 similarly to that of the first embodiment. However, in the second embodiment, only one bell crank lever 106 is disclosed. That bell crank lever 106 rotates around axle 107 and is connected by a link 108 to the link mechanism 98. An upper extension 109 to link 108 is slidably pivotally mounted to a latch 110 that is slidably received in housing 111 which extends perpendicularly from the tubular receiver 104.

In operation, when the distal end 97a of cable 97 is pushed down through the open end 105 of tubular receiver 104, it pushes down the bell crank 106 which causes lever 108 and its extension 109 to rotate around pivot 107 to both close the latch 110 over the top of the distal end 97a and move link mechanism 98 to reverse the ratcheting effect of the spring loaded reel 85. This action retracts cable 97 onto the reel 88 and further restrains the suspect or detainee around whose torso the cable is positioned. The clutch mechanism 92 cushions the retraction of the cable onto reel 88.

In the present embodiment, a tool (not shown) may be inserted through aperture 81 in cover 72 to engage the slot 109a in lever extension 109 and move it to the left to release the cable 97 from its receiver 104. In operation, the aperture 81 in cover 72 is facing downwardly when the base 71 is mounted vertically either on a wall inside a building or on a vertical surface in a police or corrections vehicle. If desired, a key or other mechanism may be fitted to operate the latch 110 and bell crank mechanism 106–109 in a secure manner. The ratcheting mechanism of the second embodiment operates somewhat similarly to the paul mechanism of the first embodiment in that it allows the cable 97 and the reel to be extended in one direction only when the cable is released from the receiver mechanism 100, and once the distal end 97a is secured in the receiver 100, the ratcheting mechanism only allows the cable 97 to be retracted or drawn up on reel 88, thus closely moving the cable around the detainee's torso.

The suspect detaining mechanism of the present invention may easily be mounted in a vertical manner on the wall of a building or correctional institution for assuring that detainees or suspects do not take advantage of a policeman or correctional officer when his or her back is turned to perform other actions within the scope of their duties. Also, the base of either detaining embodiment may be mounted on the outside of a police or corrections vehicle or may be mounted on the inside thereof to assure that detainees do not have freedom of movement around the inside of the vehicle.

While two differing embodiments of the present invention have been shown and described, it will be apparent to those skilled in the art that many changes and modifications may be made without departing from the true spirit and scope of the present invention. It is the intent of the appended claims to cover all such changes and modifications which fall within the true spirit and scope of the invention.

What is claimed:

1. A restraining device for use by law enforcement personnel to detain persons, said device comprising:
   an elongate base having first and second opposed ends and being adapted for fixed mounting on an external object,
   a cover mountable over said base including first and second apertures therethrough, each positioned adjacent one of said first and second opposed ends of said elongate base,
   an elongate resilient rod member having first and second opposed ends,
   means in communication with said resilient rod member and mounted on said frame for selectably releaseably withdrawing said resilient rod member through said first aperture on said cover, and
   selectably releasable securing means mounted on said base adjacent said second aperture for receiving and retaining said first end of said resilient rod member thereon.

2. The restraining device as defined in claim 1 wherein:
   said resilient rod member is a metal cable having a plastic sheath therearound.

3. The restraining device as defined in claim 1 wherein:
   said means for selectably releaseably withdrawing said rod member include a reel rotatably mounted on said base, a second end of said resilient rod member being affixed on said reel, for providing coiling thereon, means for biasing said reel to rotate in one of two directions and clutch means for slowing the rotation of said reel when same is rotating.

4. A restraining device mountable on a law enforcement vehicle for retaining a person by selectively releaseably securing an elongate resilient member around the torso of said person comprising:
   a frame substantially vertically mountable on a law enforcement vehicle,
   an elongate resilient rod member having one end secured adjacent one end of said restraining device and an opposing distal end of said rod member having first releasable securing means thereon,
   second selectably releasable securing means mounted on said frame adjacent an opposing end of said restraining device complementary to said first releasable securing means for receiving and retaining said first releasable securing means thereon,
   a cover mountable on said frame including a first aperture means adjacent said second releasable securing means and a second aperture means adjacent an end of said cover opposite said first aperture means, said rod member extending through said second aperture means, and
   means for selectably withdrawing said resilient rod member through said first aperture means.

5. The restraining device as defined in claim 4 wherein:
   said means for selectably withdrawing said rod member include a spring biased reel rotatably mounted on said frame,
   said reel including ratcheting means thereon for allowing selectable one-way rotation of said reel.

6. The restraining device as defined in claim 5 further including:
   clutch means engage able with said reel for slowing the withdrawal of said resilient rod member through said first aperture means.

7. The restraining device as defined in claim 5 further including:
   linking means between said reel and said second selectably releasable securing means for providing release of said spring biased reel means where said second selectably releasable securing means is not engaged by said first such means.

8. The restraining device as defined in claim 5 further including:
    linking means between said reel and said second selectably releasable securing means for providing withdrawal of said rod member through said second aperture means when said second selectably releasable securing moans is engaged by said first such means.

9. The restraining device as defined in claim 4 wherein:
    said means for selectably withdrawing said rod member include,
    pulley means through which said rod member is sheaved, said pulley means being mounted on a resiliently extensible outwardly biased shock absorber with the extension of said shock absorber acting to withdraw said rod member through said second aperture means.

10. The restraining device as defined in claim 9 further including:
    releasable ratcheting means in contact with said rod member for providing one-way movement of said rod member in the normal course of use of said restraining device.

11. The restraining device as defined in claim 4 wherein:
    a second pulley is rotatably mounted on said frame adjacent said second aperture for rotatably receiving said resilient rod member.

12. The restraining device as defined in claim 4 wherein said resilient rod member is a metal cable having a plastic sheath therearound.

\* \* \* \* \*